United States Patent [19]

Eskola et al.

[11] Patent Number: 4,906,619
[45] Date of Patent: Mar. 6, 1990

[54] ALKYL AVERMECTIN DERIVATIVES

[75] Inventors: Philip Eskola, Wall; Thomas L. Shih, Edison; Helmut Mrozik, Matawan, all of N.J.

[73] Assignee: Merck & Co., Inc., Rahway, N.J.

[21] Appl. No.: 222,868

[22] Filed: Jul. 22, 1988

[51] Int. Cl.$^4$ .................. A61K 31/70; C07H 17/04; C07D 313/06
[52] U.S. Cl. ...................... 514/30; 514/450; 536/7.1; 549/264; 71/88
[58] Field of Search .................. 514/30, 450; 536/7.1; 549/264; 71/88

[56] References Cited

U.S. PATENT DOCUMENTS

| | | | |
|---|---|---|---|
| 4,427,663 | 1/1984 | Mrozik | 536/7.1 |
| 4,713,571 | 11/1979 | Chabala et al. | 549/264 |
| 4,789,684 | 12/1988 | Goegelman | 549/264 |

OTHER PUBLICATIONS

Cram et al., *Organic Chemistry*, 2nd ed., 1964, p. 316.

*Primary Examiner*—Johnnie R. Brown
*Assistant Examiner*—Elli Peselev
*Attorney, Agent, or Firm*—David L. Rose; Hesna J. Pfeiffer

[57] ABSTRACT

There are disclosed avermectin derivatives with a hydroxy and hydrocarbon substituents at the 5, 10, 13, 23, 4' and 4" positions which are prepared by the reaction of the 5, 10, 13, 23, 4' or 4" ketone compound with an organo-metallic Grignard reagent. The compounds are potent antiparasitic and anthelmintic agents in human and animal therapy and are potent pesticidical agents against agricultural pests. Compositions containing such compounds as the active agent are also disclosed.

14 Claims, No Drawings

ALKYL AVERMECTIN DERIVATIVES

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted thereon at the 13-position with a 4-(α-L-oleandrosyl)-α-L-oleandrose group. The avermectin compounds and the instant derivatives thereof have a very high degree of anthelmintic and anti-parasitic activity.

The avermectin series of compounds isolated from the fermentation broth have the following structure:

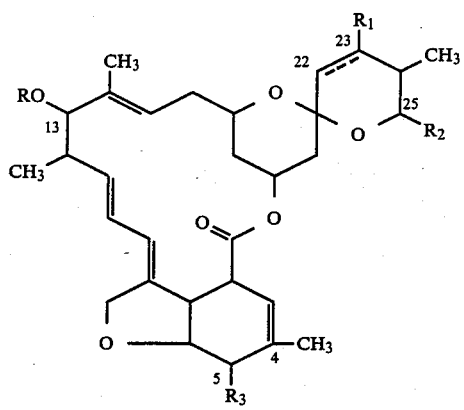

wherein R is the 4'-(α-1-oleandrosyl)-60 -1-oleandrose group of the structure:

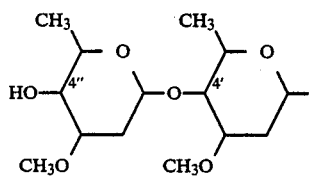

and wherein the broken line at the 22,23-position indicates a single or a double bond; $R_1$ is hydrogen or hydroxy and is present only when said broken line indicates a single bond;

$R_2$ is iso-propyl or sec butyl; and $R_3$ is methoxy or hydroxy.

There are eight different avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'(α-L-oleandrosyl)-α-L-oleandrose):

|  | $R_1$ | $R_2$ | $R_3$ |
|---|---|---|---|
| A1a | (22,23-Double Bond) | sec-butyl | —OCH$_3$ |
| A1b | (22,23-Double Bond) | iso-propyl | —OCH$_3$ |
| A2a | —OH | sec-butyl | —OCH$_3$ |
| A2B | —OH | iso-propy | —OCH$_3$ |
| B1a | (22,23-Double Bond) | sec-butyl | —OH |
| B1b | (22,23-Double Bond) | iso-propyl | —OH |
| B2 | —OH | sec-butyl | —OH |
| B2b | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

SUMMARY OF THE INVENTION

The instant invention is concerned with certan derivatives of avermect in compounds wherein certain hydroxy groups at the 5, 10, 13, 23, 4' and 4" positions are selectively oxidized to a ketone function and the ketone is treated with a Grignard reagent to result in novel compounds which are disubstituted at such positions with a hydroxy group and an alkyl, cycloalkyl, substituted alkyl or unsaturated alkyl group. Thus, it is an object of this invention to describe such compounds. It is a further object of this invention to describe the processes used to prepare such compounds. A still further object is to describe the uses of such compounds as animal antiparasitic or agricultural pesticidal agents. A still further object is to describe compositions containing such compounds as the active ingredient. Further objects will be apparent from the following description.

DESCRIPTION OF THE INVENTION

The compounds of this invention are best described in the following structural formula:

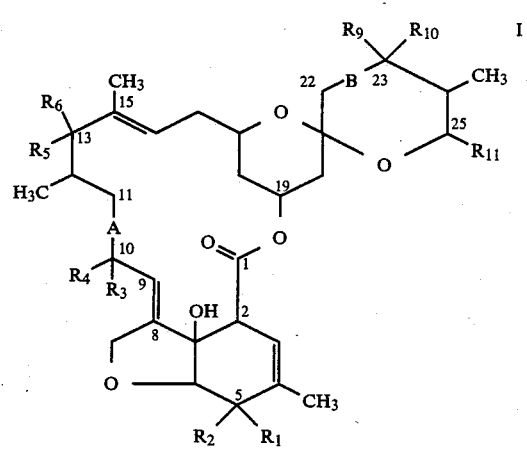

wherein A and B are independently single or double bonds;

wherein $R_1$ is hydroxy, and $R_2$ is loweralkyl, cyclo-loweralkyl, loweralkenyl or substituted loweralkyl;

or when $R_1$ is hydrogen, $R_2$ is hydroxy or methoxy;

when A is a double bond $R_4$ is not present and $R_3$ is hydrogen or loweralkyl;

when A is a single bond $R_3$ is hydroxy and $R_4$ is loweralkyl, cycloloweralkyl, loweralkenyl or substituted loweralkyl;

when $R_5$ is hydroxy, $R_6$ is loweralkyl, cycloloweralkyl, loweralkenyl or substituted loweralkyl;

or when $R_5$ is hydrogen $R_6$ is hydrogen, halogen, hydroxy,

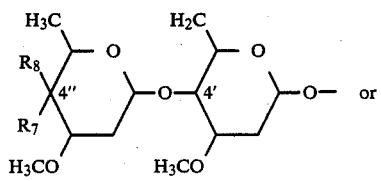

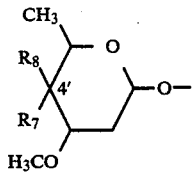

when R₇ is hydroxy and R₈ is loweralkyl, cyclolow-eralkyl, loweralkenyl, cycloloweralkyl, or substituted loweralkyl;

or when R₇ is hydrogen, R₈ is hydroxy, amino, loweralkylamino, diloweralkylamino, loweralkanoylamino, or loweralkanoyl(loweralkyl) amino;

when B is a single bond, R₉ is hydroxy and R₁₀ is loweralkyl, cycloloweralkyl, loweralkenyl, or substituted loweralkyl;

or R₉ is hydrogen and R₁₀ is hydrogen or hydroxy;

when B is a double bond R₁₀ is not present and R₉ is hydrogen; and

R₁₁ is methyl, ethyl, isopropyl, sec. butyl, or C(CH₃)=CHCH₃, —C(CH₃)=CHCH₂CH₃ or —C(CH₃)=CHCH(CH₃)₂;

provided that when R₁, R₅, R₇ and R₉ are all hydrogen and A is a double bond, R₄ is not present and R₃ is loweralkyl or provided that at the disubstituted positions 5, 10, 13, 23, 4' and 4" the combination is present whereby at least one of R₁, R₃, R₅, R₇, and R₉ is hydroxy and the corresponding R₂, R₄, R₆, R₈, and R₁₀ is loweralkyl, cycloloweralkyl, loweralkenyl or substituted loweralkyl.

In the instant invention, the term "loweralkyl": is intended to include those alkyl groups of from 1 to 6 carbon atoms of either a straight or branched chain. Exemplary of such alkyl groups are methyl, ethyl, propyl, isopropyl, butyl, sec. butyl, pentyl, hexyl and the like.

The term "cycloloweralkyl" is intended to include those cyclic alkyl groups of from 3 to 6 carbon atoms exemplified by cyclopropyl, cycloalkyl, cyclopentyl, and cyclohexyl.

The term "loweralkenyl" is intended to include those alkenyl groups of from 2 to 6 carbon atoms with one or two unsaturations and is either a straight or branched configuration. Exemplary of such alkenyl groups are ethenyl, propenyl, butenyl, butadienyl, pentenyl, isopentenyl, hexenyl and the like.

The term "substituted loweralkyl" is intended to include one or more substituents, preferably from 1 to 3 substituents on a loweralkyl group which may be selected from hydroxy, loweralkoxy or halogen.

One aspect of the preferred embodiment of the instant invention is realized in the above formula when:
A is a double bond;
B is a single or a double bond;
R₁ is a hydrogen;
R₂ is hydroxy or methoxy;
R₃ is hydrogen and R₄ is not present;
R₅ is hydrogen;
R₆ is hydrogen, hydroxy,

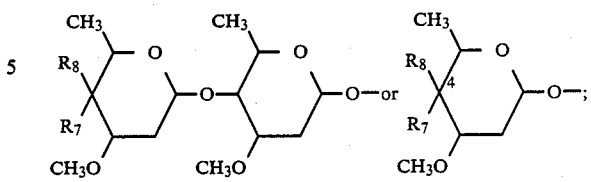

R₇, R₈, R₉ and R₁₀ are as defined in claim 1; and R₁₁ is methyl, ethyl, isopropyl or sec butyl.

Further preferred embodiments of the instant invention are realized when:
A is a double bond;
B is a single or a double bond;
R₁ and R₂ are as defined above;
R₃ is hydrogen and R₄ is absent;
R₅ is hydrogen
R₆ is

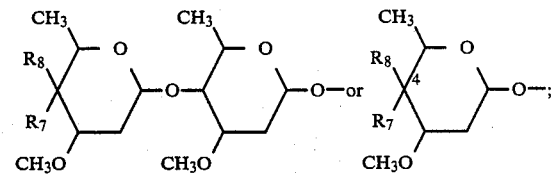

R₇, R₈, R₉ and R₁₀ are as defined in claim 1; and R₁₁ is isopropyl or sec. butyl.

Examples of preferred compounds of the invention are:
23-methyl avermectin B2a/B2b
23-methyl avermectin B2a/B2b monosaccharide
23-ethyl avermectin B2a/B2b
23-vinyl avermectin B2a/B2b
4"-methyl avermectin B1a/B1b
22,23-dihydro-4'-methyl avermectin B1a/B1b monosaccharide
22,23-dihydro-5 methyl avermectin B1a/B1b
22,23-dihydro-13-methyl avermectin B1a/B1b aglycone
22,23-dihydro-13 vinyl avermectin B1a/B1b aglycone
22,23-dihydro-13-allyl avermectin B1a/B1b aglycone
23-methyl-4"-deoxy-4"-epi-methylamino avermectin B2a/B2b
4"-epi(N-acetyl-N-methylamino)4"-deoxy-23-methyl avermectin B2a/B2b.
22,23-dihydro-4"-methyl avermectin B1a/B1b
4"-butyl-avermectin B1a/B1b
4"-ethenyl-avermectin B1a/B1b
22,23-dihydro-4"-ethenyl avermectin B1a/B1b
4"-methyl avermectin B2a/B2b
13-deoxy-23-ethenyl-avermectin B2a/B2b aglycone
13-deoxy-23-methyl-avermectin B2a/B2b aglycone The compounds of the instant invention are prepared from an organo metallic Grignard reagent, usually a magnesium compound of the formula RMgX where R is the loweralkyl, cycloloweralkkyl, loweralkenyl or substituted loweralkyl of the above structural formula and X is a halogen, preferably bromine or chlorine. The Grignard reagent is reacted with the avermectin compound with a ketone group at the 5, 10, 13, 23, 4' or 4" positions.

The disubstituted carbon atoms at the 5, 10, 13, 23, 4' or 4"-positions are assymetric and in most cases a mixture of two epimers is formed. These diastereoisomers can be separated by chromatoqraphic procedures or they can be used as a mixture of a pair of diasteromers.

The Grignard reaction follows the generalized reaction scheme of:

The following structural formula 11 is a compilation of all the Grignard reactions which may be carried out at the 5, 10, 13, 23, 4' and 4" positions, although it will be appreciated that generally all of the reactions at the possible positions are not carried out at the same time, although reactions at multiple sites are certainly possible and included within the ambit of this invention.

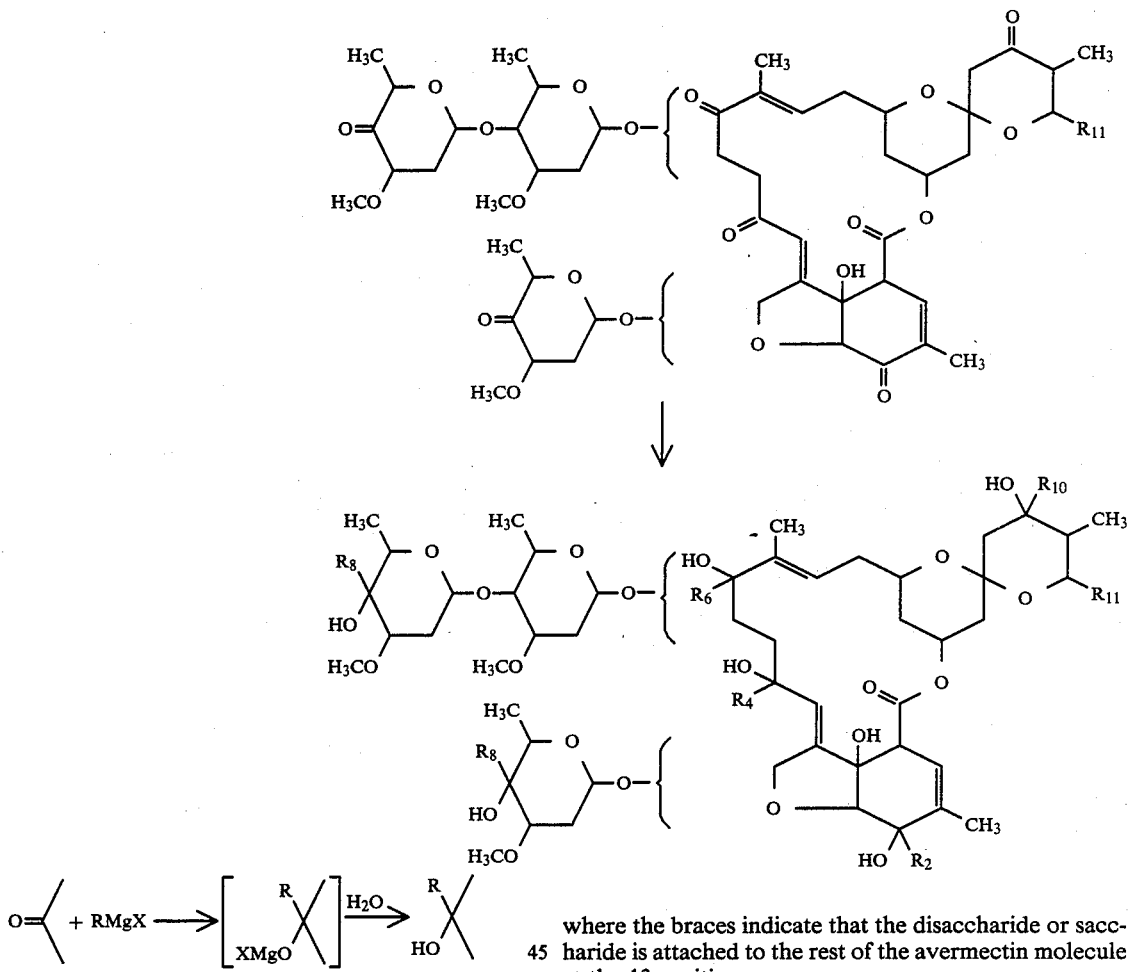

See Grignard, *Compt. Record* 130, 1322 (1900) and Wakefield *Organometal. Chem. Rev.* 1, 131 (1966).

Thus, in the above structural formula I where the starting material is, for example, a 5-keto avermectin the reaction would proceed as outlined in the following partial structural formula:

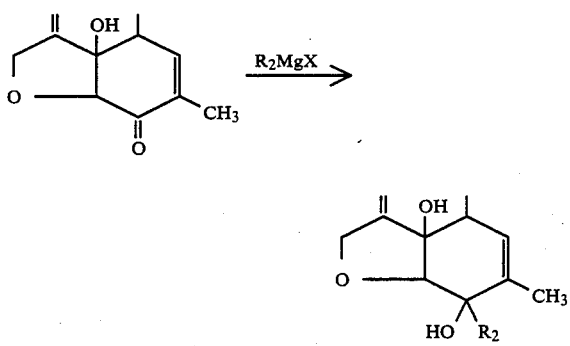

where the braces indicate that the disaccharide or saccharide is attached to the rest of the avermectin molecule at the 13-position.

The reaction is carried out under standard Grignard reaction conditions. The reaction is enerally carried out in an organic solvent such as an ether, preferably diethyl ether or tetrahydrofuran. The reaction solvents, reagents and glassware should be scrupulously dried since the Grignard reagent very readily reacts with water. For the same reasons, the reaction is carried out under a blanket of a dry, inert gas such as nitrogen. The reaction is carried out at from 0° C. to the reflux temperature of the reaction mixture although the reaction is preferably carried out at about room temperature. The reaction is complete in from about 10 minutes to 18 hours, preferably between about ½ and 3 hours, whereupon the intermediate magnesium complex is treated with water or an aqueous salt solution, such as aqueous ammonium chloride, to prepare the final product which is isolated using techniques known to those skilled in the art.

Those compounds wherein A is a double bond, $R_4$ is not present and $R_3$ is loweralkyl are prepared from the 10-hydroxy 10-loweralkyl compounds (and A is a single bond) by preparing a sulfonate ester of the 10-hydroxy group under basic conditions whereby the sulfonate ester will be eliminated along with the adjacent hydrogen to recreate the 10,11-double bond while leaving the 10-loweralkyl group intact. Preferred reagents for the preparation of the sulfonate ester are methane sulfonyl chloride, p-toluene sulfonyl chloride, trifluoromethyl sulfonyl chloride, trifluoromethyl sulfonyl anhydride and the like. The reaction is generally very rapid with the formation and elimination of the sulfonate ester occuring very quickly after its formation. Generally the reaction is carried out in an inert solvent such as tetrahydrofuran and the reaction is complete in from ½ to 5 hours when carried out at about room temperature. The preferred bases which promote the elimination of the sulfonate ester are tertiary organic amines such as triethylamine or pyridine.

PREPARATION OF STARTING MATERIALS

The ultimate starting materials for the compounds of this invention are the avermectin fermentation products defined above. Thus it is apparent that additional reactions are required to prepare the instant compounds. Specifically, reactions are carried out at the 5, 13, 22, and 23-positions and at the 10, 11 double bond. It is generally preferred to prepare whatever substituents are required at these positions before the oxidation of the hydroxy groups to the ketone groups and subsequent Grignard reaction on the thus produced ketone. Such a procedure generally avoids undesirable ide reactions. This technique is not required, however, and if desired other sequences may be used. In addition, during the oxidation and Grignard reaction described above, it is often necessary to protect the hydroxy groups at the 5-and 23-positions to avoid oxidation or substitution at such positions. With these positions protected the reactions may be carried out at the 4"- and 4' positions without affecting the remainder of the molecule. Subsequent to any of the above described reactions the protecting group may be removed and the unprotected product isolated. The protecting group employed is ideally one which may be readily synthesized, will not be affected by the reactions at the 4"- and 4'positions and may be readily removed without affecting any other functions of the molecule. One preferred type of protecting group for the avermectin type of molecule is the tri-substituted silyl group, preferably the trialkyl silyl group. One especially preferred example, is the t-butyl dimethylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours and at from 0° to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions. If it is desired to protect the 23-hydroxy group a 4", 5,23-tri(phenoxyacetyl) derivative can be prepared. Basic hydrolysis will leave the highly hindered 23-O-substituent but hydrolize the 5- and 4"-O-phenoxy acetyl groups. The 5-position is then protected as described above, selectively with a t-butyldimethylsilyl group.

The silyl group is most conveniently removed just prior to the Grignard reaction but may be removed as the final step after the other contemplated reactions are carried out. The silyl group or groups are removed by stirring the silyl compound in methanol catalyzed by an acid preferably a sulfonic acid hydrate such as methanolic 1.0% p-toluene sulfonic acid monohydrate. The reaction is complete in about 1 to 12 hours at from 0° to 50° C. Alternatively the silyl group or groups may be removed by treatment of the silyl compound with anhydrous pyridine-hydrogen fluoride in tetrahydrofuran. The reaction is complete in from 3 to 24 hours at from 0° to 25° C.

Another of the starting materials used in the foregoing reaction scheme are those in which the 22,23 double bond of the "1" type compounds has been reduced to a single bond. As is readily apparent from an analysis of the structure of avermectin starting materials there are 5 unsaturations in the 1-series of compounds. Thus in the 1-series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

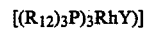

wherein $R_{12}$ is loweralkyl, phenyl or loweralkyl substituted phenyl and Y is halogen. The reduction procedure is completely described in U.S. Pat. No. 4,199,569.

The other starting materials which are used in the above reaction scheme involve the preparation of the mono-saccharide compound. That is those compounds wherein one of the α-1-oleandrosyl groups have been removed. The removal of the terminal α-1-oleandrose leaves a hydroxy group at the 4'-position which is equally amenable to the reactions described in the foregoing reaction scheme. The processes which may be used to prepare the monosaccharide derivatives of the avermectin compounds are described in U.S. Pat. No. 4,206,205. The reaction consists generally of treating the starting material disaccharide with acid in an aqueous organic solvent mixture. Water concentrations of from 0.1 to 20% by volume and acid concentrations of from about 0.01 to 0.1% will predominantly produce the monosaccharide product.

A further procedure for the preparation of the monosaccharide utilizes a 1% mineral acid solution in isopropanol at for 20°–40° C. preferably at room temperature for from 6 to 24 hours. Mineral acids such as sulfuric, hydrohalic, phosphoric and the like may be employed.

Some of the compounds of the instant invention differ from other avermectin compounds in that the 10,11 double bond is reduced. The effect of reducing the 10,11 double bond is that the conjugated diene system is broken. The elimination of the conjugated double bonds has a considerable effect on the ultraviolet absorption characteristics of the molecule and has resulted in a surprising and very significant increase in the stability of the molecule when it is exposed to ultraviolet light, as well as ordinary sunlight which has a significant component of ultraviolet light. This increased stability in the presence of ultraviolet light makes these compounds particularly suited to agricultural applications and also to topical animal applications where photoinstability would be detrimental to the optimum performance of each compound.

The 10,11 double bond of the avermectin starting materials is either reduced catalytically or is chemically modified. The catalytic reduction is carried out using platinum group metals as catalysts such as platinum, palladium, rhodium, and the like. Generally, the metal catalyst is dispersed on nd supported on a substrate such as powdered carbon. The reaction is carried out under a blanket of hydrogen gas either at atmospheric pressure or pressurized up to 10 atmospheres (gauge) of hydrogen pressure in pressurable equipment ordinarily used for such reactions. The reaction is carried out in a solvent which is stable to the hydrogenation conditions and which will not adversely affect the catalyst. Lower alkanols, such as methanol, ethanol, isopropanol and the like, ethyl acetate, cyclohexane, and the like are suitable. The reaction is generally carried out at room temperature although temperature as high as 50° C. are suitable and under such conditions the reaction is complete in from 1 to 24 hours. If the hydrogenation apparatus is so equipped, the progress of the reaction may be followed by observing the amount, either in volume or in pressure drop, of hydrogen that is consumed. The products are isolated using techniques known to those skilled in the art.

The catalytic hydrogenation process generally yields a mixture of products since the avermectin starting materials have three or four double bonds which may be hydrogenated. This would include the 3,4 and 22,23 double bonds. The 14,15 double bond is sterically hindered and generally requires more vigorous reaction conditions than are described above in order to effect hydrogenation. The various hydrogenation products are isolated from the mixture of reaction products using standard techniques such as fractional crystallization and chromatography. The double bonds which are desired to be retained in the final product may be protected to render them inert during the hydrogenation procedure. When the hydrogenation is complete, the double bond may be regenerated by removing the protecting groups.

The 10,11 double bond may also be reacted chemically and in the process various substituents at the 10 position ($R_3$ and $R_4$) are introduced according to the following reaction scheme where only the furan ring and carbon atoms 6 to 12 are shown in the partial structural formulas.

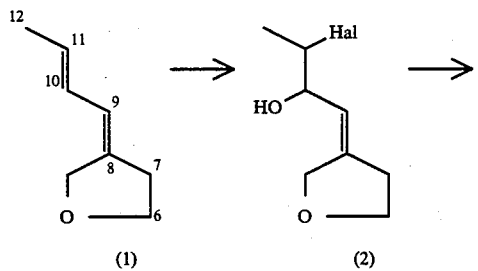

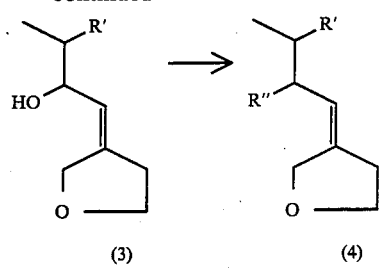

wherein $R'$, and $R''$ are as defined above and Hal is a halogen.

Partial structure (1) is reacted with a reagent capable of preparing a halohydrin group (a 10-hydroxy, 11-halo function). Various reagents and reaction conditions are capable of preparing a halohydrin such as N-haloacetamide, N halosuccimide, addition of hydrochloric acid to an epoxide, and the like. Bromine is the preferred halogen. When reagents such as N haloacetamide and N halo succinimide are used, the reaction is carried out in an inert solvent, such as acetone, ether, tetrahydrofuran, and the like. The reaction is generally carried out at from −20° to 50° C. and is complete in from 30 minutes to 24 hours and is generally carried out in the dark.

The halohydrin compound (2) may be treated with a reducing agent, such as a trialkyltin hydride to displace the halogen with a hydrogen. Partial structures (2) and (3), with the 11 position substituent being a halogen or hydrogen constitutes the definition of $R''$ as shown in partial structure (3). Further reactions are possible at the 10-position to convert the hydroxy group to other groups (partial structure (4)) using techniques known to those skilled in the art.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasties of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidoqyne spp. which may be of importance in agriculture The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active avermectin compounds are intimately dispersed throughout the carrier by methods such as grinding, stirring, milling or tumbling. Compositions containing from about 0.005 to 2.0% by weight of the active compound are particularly suitable as feed premixes Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene qlycol, silica; disintegrants, for example, potato starch, acceptable wetting agents such s sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 0.1 to about 5 mg of active ingredient per kg. of body weight of the subject in one or more treatments per day. A preferred daily dosage for adult humans lies in the range of from about 0.1 to 20 mg. of active ingredients per kg. of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 5 mg. to about 50 mg. of the active ingredient; however, in general, it is preferable to employ a dosage amount in the range of from about 5 mg to 100 mg. In parenteral administration, the unit dosage is usually the pure compound I in sterile water solution or in the form of a soluble powder intended for solution.

In the isolation of the avermectin compounds, which serve as starting materials for the instant process, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec butyl group and an iso propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ratio of about 80% avermectin B1a or A1a and 20% avermectin B1b or A1b. Thus the preferred composition of this invention is one which contains more than about 80% of the "a" component and less than about 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

In the following examples, the various starting materials therefor are avermectin compounds or derivatives of avermectin compounds. The avermectin compounds and the preparation and isolation thereof from fermentation broths are described in U.S. Pat. No. 4,310,519 issued Jan. 12, 1982. The 4"- and 4'-keto starting materials are described in U.S. 4,427,663. The selective 22,23-dihydro derivatives of avermectin compounds are described in U.S. Pat. No. 4,199,569 issued Apr. 22, 1980. The monosaccharide derivatives of avermectin compounds are described in U.S. Pat. No. 4,206,205 issued Jan. 3, 1980.

EXAMPLE 1

23 Methylavermectin B2a and/or B2b.

A solution of 250 mg of 23-oxoavermectin B2a/B2b in 12 ml of anhydrous tetrahydrofuran was stirred under nitrogen at room temperature while 0.5 ml of a 2.85 molar methylmagnesium bromide solution in ether was added dropwise from a syringe. After 1 hour the reaction mixture was poured onto 60 ml of a 10 % aqueous ammonium chloride solution, and the product was extracted with ethyl acetate. The extract was washed with water, dried over $MgSO_4$, and concentrated in vacuo to 210 mg of yellow glass. This was purified by preparative layer silica gel chromatography with methylene chloride containing 3 to 5 % of methanol to give 155 mg white foam. It was further purified by preparative high performance liquid chromatography on a reverse phase column (Whatman M20 Partisil 10/50 ODS -3) with a methanol-$H_2O$ 85:15 solvent mixture to give 81 mg of 23 methylavermectin B2a and/or B2b, which was characterized by its mass spectrum (m/e+: 904=M+, 337, 319) and $^1$H-NMR spectrum.

EXAMPLE 2

23-Methylavermectin B2a and/or B2b monosaccharide.

When 35 mg of 23 oxoavermectin B2a and/or B2b monosaccharide was reacted according to the procedure fully described in example 1, 15 mg of 23-methylavermectin B2a and/or B2b monosaccharide was obtained as a white foam, which was characterized by its mass spectrum (m/e+: 742 =M+-18, 337, 319) and $^1$H-NMR spectrum.

EXAMPLE 3

23-Ethylavermectin B2a and/or B2b.

A solution of 90 mg of 23-oxoavermectin B2a/B2b in 7 ml of anhydrous ether was stirred under nitrogen in an ice bath while 0.3 ml of a 2.0 molar ethylmagnesium bromide in tetrahydrofuran solution was added dropwise from a syringe. After 30 minutes the reaction mixture was stirred at room temperature, and after 90 min. an additional 0.4 ml of ethyl magnesium bromide solution was added. After a total reaction time of 2 hours the mixture was poured onto 50 ml of a 10 % aqueous ammonium chloride solution, and the product was extracted with ether. The extract was washed with water, dried over magnesium sulfate and concentrated in vacuo to 80 mg of light colored glass. This was purified by preparative high performance liquid chromatography on a reverse phase column (Whatman M9 Partisil 10/50 ODS -3) with a MeOH-$H_2O$ 85:15 solvent mixture to give 14 mg of 23-ethylavermectin B2a and/or B2b, which was characterized by its mass spectrum (m/e+: 612=M+-306, 351, 333) and $^1$H-NMR spectrum.

EXAMPLE 4

23-Vinylavermectin B2a and/or B2b.

A solution of 90 mg of 23-oxoavermectin B2a/B2b in 7.5 ml of anhydrous ether was stirred under nitrogen in an ice bath while 0.3 ml of a 1.7 molar vinylmagnesium bromide in tetrahydrofuran solution was added dropwise from a syringe. After 30 minutes the reaction mixture was stirred at room temperature, and an additional 0.3 ml of vinylmagnesium bromide solution was added. After a total reaction time of 90 minutes the mixture was poured onto 50 ml of a 10% aqueous ammonium chloride solution, and the product was extracted with ethyl acetate. The extract was washed with water, dried over magnesium sulfate, and concentrated in vacuo to 90 mg of light foam. This was purified by preparative high performance liquid chromatography on reverse phase column (Whatman M9 Partisil 10/50 ODS-3) with a methanol -$H_2O$ 85:15 solvent mixture to give 15 mg of 23-vinylavermectin B2a and/or B2b, which was characterized by its mass spectrum (m/e+: 898=M+18, 610=M+-306, 349, 331) and $^1$H -NMR spectrum.

EXAMPLE 5

4"-Methylavermectin B1a and/or B1b.

A solution of 110 mg of 4"-oxoavermectin B1a/B1b in 7.0 ml of anhydrous ether was stirred under nitrogen in an ice bath while 0.25 ml of a 2.85 molar methylmagnesium bromide in ether solution was added dropwise from a syringe. After 20 minutes the reaction mixture was poured onto 30 ml of a 10% aqueous ammonium chloride solution, and the product was extracted with ethyl acetate. The extract was washed with water, dried over magnesium sulfate, and concentrated in vacuo to 90 mg of yellow glass. Purification via preparative layer silica gel chromatography with methylene chloride containing 4% of MeOH gave 75 mg of a glass, which showed three peaks by high performance liquid chromatography. Separation via preparative HPLC on a reverse phase column (Whatman M20 Partisil 10/50 ODS -3) with a methanol-$H_2O$ 85:15 solvent mixture gave 12 and 13 mg respectively of the two 4"-epimers of 4"-methyl-avermectin B1a and/or B1b, which were characterized by their mass spectra (m/e+: 868=M+-18, 159 =145+14) and $^1$H NMR spectrum.

EXAMPLE 6

22,23-Dihydro 4'-methylavermectin B1a and/or B1b monosaccharide.

When 22,23-dihydro 4'-oxoavermectin B1a and/or B1b monosaccharide was reacted and isolated according to the procedure described in example 5 the two 4'-epimers of 22,23 dihydro-4"-methylavermectin B1a and/or B1b were obtained, which were characterized by their mass and $^1$H-NMR spectra.

EXAMPLE 7

2,23-Dihydro -5-methylavermectin B1a and/or B1b.

A solution of 90 mg of 22,23-dihydro-5-oxoavermectin B1a/B1b in 5.0 ml of anhydrous ether was stirred under nitrogen in an ice bath while 0.2 ml of a 2.8 molar methylmagnesium chloride in tetrahydrofuran solution was added dropwise from a syringe. After 25 minutes the reaction mixture was poured onto cold aqueous ammonium chloride solution, and the product was extracted with ethyl acetate. The extract was washed with water, dried over magnesium sulfate, and concentrated in vacuo to 100 mg of yellow foam. Purification via preparative silica gel layer chromatography with methylene chloride containing 4% of methanol and extraction of the appropriate band gave 20 mg of one of the two C -5 epimeric 22,23-dihydro -5-methylavermectin B1a and/or B1b aglycone as a white glass. A second band of slightly slower moving material than the first epimer was further purified by repeated silica gel preparative layer chromatography with methylene chloride containing 3% methanol to give 21 mg of the other C -5 epimeric product. Both compounds were characterized by mass and $^1$-HNMR spectrometry.

EXAMPLE 8a

5-O-tert-Buthyldimethylsilyl-22,23-dihydro-13-methyl-avermectin avermectin B1a and/or B1b aglycone.

A solution of 500 mg of 5-tert butyldimethylsilyl-22,23-dihydro-avermectin B1a and/or B1b aglycone in 30 ml of ether was stirred under nitrogen in an ice bath. Then 1.0 ml of a methyl magnesium chloride solution (2.8 molar in tetrahydrofuran) was added. After 10 minutes of stirring the reaction mixture was poured into an aqueous ammonium chloride solution, and the product was extracted with ether. The ether extract was washed with water, saturated aqueous sodium chloride, dried over magnesium sulfate and concentrated in vacuo to 510 mg of crude 5-O-tert-butyldimethylsilyl 22,23-dihydro-13-methyl avermectin B1a and/or B1b aglycone as a yellow foam, which was characterized by its mass spectrum (m/e : 696=M$^+$- H$_2$O, 321 =307 peak+CH2) and $^1$H-NMR spectra (new methyl peak at 1.3 PPM).

EXAMPLE 8b 22,23-Dihydro-13-methyl-avermectin B la and/or B lb aglycone.

A solution of 490 mg of crude 5-O-tert butyl-dimethylsilyl-22,23-dihydro-13-methyl-avermectin B la and/or B1b aglycone and 500 mg of p-toluenesulfonic acid in 50 ml of methanol was held at room temperature for 35 minutes and then poured into 130 ml of dilute aqueous sodium bicarbonate solution. The product was extracted with ether and ethyl acetate. The extract was washed with water, saturated aqueous sodium chloride, dried over magnesium sulfate and concentrated in vacuo to 420 mg of yellow foam. Purification by preparative silica gel thin layer chromatography with a methylene chloride nitrogen-ethyl acetate 85:15 solvent mixture afforded 350 mg of pure 22,23-dihydro-13-methyl-avermectin B1a and/or B1b aglycone, which was characterized by its mass spectrum (m/e : 600=M$^+$, 321=base peak=307 fragment+CH$_2$) and $^1$H-NMR (new methyl at 1.29 PPM) spectra. It was crystallized from CH$_2$Cl$_2$: mp 149°-152°, [α]D = +87.2° (acetone).

EXAMPLE 9a

5-O-tert-Butyldimethylsilyl-22,23-dihydro-13-vinyl avermectin B1a and/or B1b aglycone.

A solution of 70 mg of 5-O-tert-butyldi-methylsilyl-22,23-dihydro-avermectin B1a and/or B1b aglycone in 5 ml of ether was reacted with 0.22 ml of an 1.7 molar solution of vinyl magnesium bromide in tetrahydrofuran and worked up according to the procedure of example 8a to give 80 mg of crude 5-O-tert-butyldimethylsilyl-22,23-dihydro-13-vinylavermectin B1a and/or B1b aglycone, which was characterized by its mass spectrum (m/e : 708=M$^+$-H$_2$O, 651=M$^+$-H$_2$O-C$_4$H$_9$, 484=458 fragment+C=CH$_2$) and $^1$H-NMR spectra.

EXAMPLE 9b 22,23-Dihydro-13-vinylavermectin B1a and/or B1b aglycone.

80 Mg of crude 5-O-tert butyldimethylsilyl-22,23-dihydro-13-vinylavermectin B1a and/or B1b aglycone was deprotected according to the procedure fully described in example 8b using 80 mg of p-toluenesulfonic acid and 8 ml of methanol and purified by preparative silica gel thin layer chromatography with a methylene chloride nitrogen-ethyl acetate-methanol 82:15:3 solvent mixture to give 40 mg of 22,23-dihydro 13 vinylavermectin B1a and/or B1b aglycone, which was characterized by its mass spectrum (m/e : 594.357 =M$^+$-H$_2$O, 333=307 fragment +C=CH$_2$) and $^1$H-NMR spectra. It was crystallized from CH$_2$Cl$_2$, mp 154°-156°.

EXAMPLE 10a

5-O-tert Butyldimethylsilyl-22,23-dihydro -13-allylavermectin B1a and/or B1b aglycone.

A solution of 70 mg of 5-O-tert-butyldimethylsilyl-22,23-dihydro avermectin B1a and/or B1b aglycone in 5 ml of ether was reacted with 0.1 ml of an 2.6 molar solution of allyl magnesium chloride in tetrahydrofuran and worked up according to the procedure of EXAMPLE 8a to give 70 mg of light foam. Purification by preparative silica gel thin layer chromatography with methylene chloride nitrogen as solvent afforded 45 mg of pure 5-O-tert-butyldimethyl silyl -22,23-dihydro -13 allylavermectin B1a and/or B1b aglycone, which was characterized by its mass spectrum (m/e: 740=M$^+$, 722=M$^+$-H$_2$O, 347=307 fragment+CHCH=CH$_2$) and $^1$H-NMR spectra (showing additional vinylic protons).

EXAMPLE 10b 22,23-Dihydro -13 -allylavermectin B1and/or B1b aglycone.

45 Mg of crude 5-O-tert-butyldimethylsilyl 22,23 dihydro 13 allylavermectin B1a and/or B1b aglycone was deprotected according to the procedure fully described in example 8b using 45 mg of p-toluenesulfonic acid and 5 ml of methanol, and was purified by preparative silica gel thin layer chromatography with a methylene chloride nitrogen-ethyl acetate 90:10 solvent mixture to give 20 mg of 22,23-dihydro -13-allylavermectin B1a and/or B1b aglycone, which was characterized by its mass spectrum (m/e : 626 =M$^+$H$_2$O, 347=307 fragment +CHCH=CH$_2$) and $^1$H-NMR spectra.

EXAMPLE 11

5-O-t-Butyldimethylsilyl-23-methylavermectin B2a and/or B2b.

A solution of 500 mg of 23methylavermectin B2a and/or B2b, 240 mg of imidazole and 240 mg of tert-butyldimethylsilyl chloride in 4 ml of anhydrous dimethyl formamide is stirred at room temperature for 50 minutes. Then the reaction mixture is poured into 150 ml of ice cold water and the aqueous phase is extracted four times with 20 ml of ether. The organic phase is washed twice with water, aqueous sodium chloride solution, dried with magnesium sulfate and concentrated in vacuo to a white foam. The crude product is purified by silica gel column chromatography with a methylene chloride nitrogen ethyl acetate 90:10 to 70:30 solvent system to give 5-O-butyldimethylsilyl-23-methylavermectin B2a and/or B2b as an amorphous foam, which is characterized by its $^1$H-NMR- and mass spectra.

EXAMPLE 12

5-O-t-Butyldimethylsilyl-23-methyl-4"-oxoavermectin B2a and/or B2b.

To a solution containing 0.091 ml of oxalyl chloride in 2.3 ml of dry methylene chloride nitrogen stirred at $-60°$ C. is added 0.015 ml of dry dimethylsulfoxide dissolved in 1.2 ml of dry methylene chloride nitrogen during 15 min. Then a solution of 465 mg of 5-O-t-butyldimethylsilyl-23-methylavermectin B2a and/or B2b dissolved in 2.3 ml of dry methylene chloride nitrogen is added over a period of 15 minutes while maintaining the temperature at $-60°$ C. The reaction mixture is stirred at this temperature for 30 minutes when 0.065 ml of dry triethylamine is added. The mixture is stirred for 5 additional minutes at $-60°$ C., and then the cooling bath is removed and the reaction mixture is allowed to come to ambient temperature. After addition of water the reaction product is extracted with $CH_2Cl_2$, the extract is washed with water, dried and concentrated in vacuo to a yellow foam. This is identified by its mass and NMR spectra as 5-O-t-butyldimethylsilyl 23-methyl-4"-oxoavermectin B2a and/or B2b, which is used for further chemical reactions without purification.

EXAMPLE 13

5-O-t-Butyldimethylsilyl-23-methyl 4"-deoxy-4"-epimethylaminoavermectin B2a and/or B2b.

A solution of 0.026 ml of glacial acetic acid in 3.0 ml of methanol is treated with methylamine gas at 0° C. until the pH of the solution reaches 9.0. To this a solution containing 445 mg of 5-O-t-butyldimethylsilyl-23-methyl-4"-oxoavermectin B2a and/or B2b in 2.0 ml of methanol is added, and the reaction mixture is stirred at room temperature for 1 hour, when a solution of 350 mg of sodium cyanoborohydride in 0.075 ml of methanol is added slowly over 10 min. After 50 min the reaction mixture is poured into 150 ml of cold aqueous sodium carbonate solution and the product is extracted with ether. The extract is washed with water, dried, and concentrated in vacuo to a yellow foam. Thin layer chromatography (silica gel, methylene chloride nitrogen-ethyl acetate 85:15) of the crude product at this point will show several spots. Further purification by silica gel column chromatography using methylene chloride nitrogen ethyl acetate solvent mixtures gives as major reaction product 5-O-t-butyldimethylsilyl-23-methyl-4"-deoxy-4"-epi-methylamino avermectin B2a and/or B2b, accompanied by small amounts of 5-O-t-butyldimethylsilyl-23-methyl-4"-deoxy-4"-methylaminoavermectin B2a and/or B2b, and, 5-O-t-butyldimethylsilyl-23-methyl-4"-epi-avermectin B2a and/or B2b as light foams, which are characterized by their mass and $^1$H-NMR spectra.

EXAMPLE 14

23-Methyl-4"-deoxy-4"-epi-methylaminoavermectin B2a and/or B2b.

A solution of 140 mg of 5-O-t-butyldimethylsilyl-23-methyl-4"-deoxy-4"-epi- methylaminoavermectin B2a and/or B2b in 2.0 ml of methanol and a solution of 70 mg of p-toluenesulfonic acid monohydrate in 5.0 ml of methanol is mixed and stirred at room temperature for 45 minutes, and then poured into dilute aqueous sodium bicarbonate solution. The product is extracted with ethyl acetate, washed with water and dried over magnesium sulfate, concentrated in vacuo, and purified by preparative silica gel column chromatography with a methylene chloride nitrogen-methanol 95:5 solvent mixture to give 23-methyl -4"-deoxy-4"-epi-methylaminoavermectin B2a and/or B2b, which is identified by NMR and mass spectra.

EXAMPLE 15

4"-epi-(N-Acetyl-N-methylamino)-4"-deoxy-5-O-t-butyl dimethylsilyl-23-methylavermectin B2a and/or B2b A solution of 100 mg of 5-O-t-butyldimethyl-silyl-23-methyl-4"-deoxy-4"-epi-methylaminoavermectin B2a and/or B2b, 100 μl of ethyl diisopropylamine in 1.5 ml of methylene chloride nitrogen is treated with 8 μl of acetyl chloride and stirred at room temperature for several hours. Then it is poured onto ice, extracted with methylene chloride nitrogen, washed with aqueous sodium bicarbonate, dried and concentrated in vacuo to a light solid. Purification by preparative silica gel layer chromatography with methylene chloride nitrogen +1% of methanol gives as a white solid, which is characterized by its mass and $^1$H-NMR spectra.

EXAMPLE 16

4"-epi-(N-Acetyl-N-methylamino)-4"-deoxy-23-methylavermectin B2a and/or B2b

A solution of 70 mg of 4"-epi(N-acetyl-N-methylamino)-4"-deoxy-5-O-t-butyldimethylsilyl -23-methylavermectin B2a and/or B2b in 1.0 ml of methanol and a solution of 35 mg of p-toluenesulfonic acid monohydrate in 2.5 ml of methanol is mixed and stirred at room temperature for 45 minutes, and then poured into dilute aqueous sodium carbonate solution. The product is extracted with ethyl acetate, washed with water and dried over magnesium sulfate, concentrated in vacuo, and purified by preparative silica gel column chromatography with a methylene chloride nitrogen-methanol 95:5 solvent mixture to give 4"-epi-(N-acetyl N-methylamino)-4"deoxy-23-methylavermectin B2a and/or B2b, which is identified by its NMR and mass spectra.

EXAMPLE 17a

5-O-t-Butyldimethylsilyl-10,11-dihydro-10-hydroxy-11-bromoavermectin B1a/1b.

To a solution of 500 mg of 5-O-t-butyldimethylsilyl avermectin B1a/1b in 10 mL of acetone and 1 mL of water was added 110 mg of N-bromoacetamide in one portion. The mixture was stirred at 20° C. in the dark for 1 hour. The mixture was then poured into a separatory funnel containing 100 mL of water and subsequent extraction with ether afforded the crude product. Preparative layer chromatography using three 0.1 mm thick silica gel plates eluted in 60% ethyl acetate in hexane provided 180 mg of product (Rf=0.4) which was characterized by its NMR and mass spectra.

NMR(200 mHz): 0.14 (s), 0.94 (s), 1.18 (d, J=7 Hz), 1.24 (D, J=6 Hz), 1.25 (d, J=6 Hz), 1.51 (m), 1.59 (s), 1.82 (s), 3.18 (t, J=9 Hz), 3.24 (t, J=9 Hz), 3.41 (s), 3.45 (s), 3.45 (m), 3.80 (m), 3.82 (d, J=5 Hz), 4.04 (m), 4.30 (br m), 4.45 (br s), 4.54 (s), 4.72 (d, J=2 Hz) 4.72 (ABq, J=16 Hz), 5.24 (br d, J=8 Hz), 5.33 (s), 5.40 (d, J=2 Hz, 5.40 (m), 5.58 (dd, J=3, 10 Hz), 5.80 (dd, J=2, 10 Hz), 5.86 (br s).

EXAMPLE 17b

5-O-tert-Butyldimethylsilyl-10,11-dihydro-10-hydroxy avermectin B1a/1b

A solution of 168 mg of 5-O-tert butyldimethylsilyl-10,11-dihydro-10-hydroxy-1-bromoavemectin B1a/1b in 6 mL of toluene and 0.4 mL of tri-n-butyltinhydride was heated in a 100° C. oil bath under nitrogen for 2 hours. The mixture was then cooled to 20° C. and flash chromatographed through a column of 50 g of silica gel eluting with dichloromethane, then 1:1 hexane:ethyl acetate. Final HPLC purification (Whatman Partisil M20 10/50 ODS-3 column, 90:10 methanol:water) afforded 60 mg of pure 5-O-tert-butyldimethyl-silyl-10,11)dihydro-10-hydroxy avermectin B1a/1b characterized by its NMR and mass spectra. 200 MHz NMR: 0.15 (s), 0.95 (s), 1.11 (d, J=7 Hz), 1.14 (d, J=6 Hz), 1.26 (d, J=6 Hz), 1.30 (d, J=6 Hz), 1.55 (s), 1.55 (m), 1.81 (s), 2.0 (m), 2.19 (s), 2.2–2.5 (m), 2.54 (d, J=2 Hz), 3.19 (t, J=9 Hz), 3.26 (t, J=9 Hz), 3.36 (s), 3.44 (s), 3.48 (s), 3.50 (m), 3.66 (d, J=6 Hz), 3.80 (m), 4.03 (br s, m), 4.40 (br s), 4.50 (br s), 4.76 (d, J=2 Hz), 4.80 (ABq, J=15 Hz), 5.00 (br s), 5.28 (s), 5.30 (s), 5.38 (s), 5.43 (d, J=3 Hz), 5.44 (m), 5.60 (dd, J=3,10 Hz), 5.80 (dd, J=2,10 Hz).

EXAMPLE 17c

5-O-tert-butyldimethylsilyl-10-oxo-11-hydro-avermectin B1a/1b

A solution of 800 mg of 5-O-t-butyldimethyl-silyl-10,11-dihydro-10-hydroxyavermectin B1a/1b in 12 mL of dichloromethane was stirred with 1 g of celite and 1.3 g of pyridinum chlorochromate at 20° C. for 5 hours. The dark slurry was then filtered through a pad of silica gel using 1:1 hexane:ethyl acetate as eluant. Evaporation of the solvent afforded 678 mg of 5-O-tert-butyl-dimethylsilyl-10oxo-11-hydroavermectin B1a/1b characterized by its NMR and mass spectra.

200 MHz NMR: 0.14 (s), 0.92 (s), 1.16 (d, J=7 Hz), 1.26 (d, J=6 Hz), 1.28 (d, J=6 Hz), 1.53 (s), 1.55 (m), 1.80 (s), 2.30 (m), 2.60 (s), 3.16 (t, J=9 Hz), 3.24 (t, J=9 Hz), 3.32 (d, J=2 Hz), 3.42 (s), 3.44 (s), 3.45 (m), 3.68 (m), 3.84 (d, J=6 Hz), 3.86 (s), 4.44 (br s), 4.74 (d, J=3 Hz), 4.89 (d, J=3 Hz), 4.96 (s), 5.00 (m), 5.26 (d, J=2 Hz), 5.40 (d, J=3 Hz), 5.50 (m), 5.56 (dd, J=3, 10 Hz), 5.78 (dd, J=2, 10 Hz), 6.12 (s).

EXAMPLE 17d

5-O-tertbutyldimethylsilyl-4″,7-di-O-trimethylsilyl-10-oxo-11-hydroavermectin B1a/1b To 1.1 g of ·5-O-tertbutyldimethylsilyl-10-oxo-11-hydroavermectin B1a/1b in 5 mL of dimethylformamide at 22° C. was added 2 mL of bis-trimethylsilyltrifluoroacetamide (BSTFA). The mixture was stirred at 22° C. for 16 hours before the solvent was removed in vacuo. The residual solid was filtered through a column of silica gel with 20% ethyl acetate in hexane. The filtrate was evaporated in vacuo to afford 1.2 g of 5-O-tertbutyldimethylsilyl-4″,7-di -O-trimethylsilyl-10-oxo-11-hydroavermectin B1a/1b characterized by the pressure of a trimethylsilyl signal at 0.13 ppm of the NMR and its mass spectra.

EXAMPLE 17e

5-O-tertbutyldimethylsilyl-4″,7-di-O-trimethylsilyl-10-hydroxy-10-methyl-10,11-dihydro avermectin B1a/1b To a solution of 379 mg of 5-O-tertbutyl-dimethylsilyl-4″,7-di-O-trimethylsilyl-10-oxo-11-hydroavermectin B1a/1 in 10 mL of distilled THF at −78° C. was added 1.5 mL of a 3.2 M methyl magnesium bromide solution in ether. The mixture was stirred at 0° C. for 2.5 hours before 3 mL of a saturated ammonium chloride solution was added to stop the reaction. Thin layer silica gel chromatographic analysis indicated a new uv-inactive product with an $R_f$ of 0.25 in 20% ethyl-acetate hexane. The reaction mixture was combined with 50 mL of pH7 buffer and extracted with ether. The ethereal extracts were combined, dried over MgSO4, and evaporated in vacuo to yield a solid. Purification of this solid by preparative layer chromatography (PLC) afforded 217 mg of 5-O-tertbutyldimethylsilyl-4″,7-di-O-trimethylsilyl-10,11-dihydro-10-hydroxy-10-methylavermectin B1a/1b. Its NMR spectrum showed the presence of the new methyl group as a singlet at 1.32 ppm and the upfield shift of the C9 proton from 6.12 to 5.55 ppm.

EXAMPLE 17f

10-Methyl-10-hydroxy-10,11-dihydroavermectin B1a/1b

To a solution of 58 mg of 4″,7-di-O-trimethylsilyl-O-tertbutyldimethylsilyl-10-methyl-10-hydroxy 10,11-dihydroavermectin B1a/b in 1 mL of THF in a stoppered polypropylene vial was added 6 mL of HF pyridine solution (prepared by diluting 10 mL of commercially available HF pyridine complex with 20 mL of dry pyridine and 70 mL of THF). The reaction was stirred at 22° C. for 18 hours and then diluted with ice water. The hydrofluoric acid was neutralized with aqueous sodium bicarbonate and the organic product was extracted with ether. The ethereal extracts were combined, dried over MgSO4, and evaporated in vacuo to yield a glossy solid. PLC on two 0.5 mm silica gel plates eluted in ethyl acetate provided 36 mg of 10-methyl-10-hydroxy-10,11-dihydrovermectin B1a/1b characterized by its NMR and mass spectra.

EXAMPLE 17g

5-O-tertbutyldimethylsilyl-4″,7-di-O-trimethylsilyl-10-methylavermectin B1a/1 b

To a solution of 127 mg of 5-O-tertbutyldimethyl silyl-4″,7-di-O-trimethylsilyl-10-hydroxy-10-methyl-10,11-dihydroavermectin B1a/1b in 4 mL of THF and 0.5 mL of distilled triethylamine was added 0. 170 mL of methanesulfonyl chloride. After 1 hour the cloudy mixture was loaded onto two 1000 micron thick silica gel plates and the plates were eluted in 20% ethyl acetate in hexane. Extraction of the appropriate band provided 42 mg of 5-O-tertbutyldimethylsilyl-4″,7-di-O-trimethylsilyl-10-methylavermectin B1a/1b characterized by its NMR and mass spectra.

NMR (300 MHz): new vinylic methyl group at 1.78 ppm next to the C$_4$ methyl at 1.74 ppm, C$_{11}$H at 5.75 ppm.

EXAMPLE 17h

10-Methylavermectin B1a/1b

To a solution of 33 mg of 5-O-tert-butyldimethylsilyl-4'',7-di-O-trimethylsilyl-10-methyl avermectin B1a/B1b in 2 mL of THF was added 2 mL of hydrogen fluoride-pyrimidine solution (same as in Example 17f). After 16 hours at 22° C. the solution was poured into a separatory funnel containing ice water and the hydrofluoric acid was neutralized with sodium bicarbonate. The organic product was extracted from the aqueous phase with ether. The ethereal extracts were combined and dried over MgSO$_4$ and evaporation of the solvent in vacuo provided a solid. PLC on two 0.5 mm silica gel plates in 75% ethylacetate hexane afforded 21 mg of pure 10-methylavermectin B1a/1b characterized by its NMR and mass spectra.

EXAMPLE 18a

4''-Vinyl-5-O-tert-butyldimethylsilylavermectin B1a/1b

To 0.9 mL of a 1.6 M vinyl Grignard solution in tetrahydrofuran was added 9 mL of distilled tetrahydrofuran. The solution was cooled to 0° C. before a solution of 100 mg of 4''-oxo-5-O-tert-butyldimethylsilyl avermectin B1a/B1b in 0.5 mL of THF was added dropwise. After 15 min, analysis by thin layer chromatography indicated all starting material to be reacted. The reaction was quenched after 30 min by the addition of 5 mL of ammonium chloride solution and the product was extracted with ether. The ether extracts were combined, dried over MgSO$_4$ and evaporated in vacuo to afford a glossy solid. Preparative layer chromatography on two 0.05 mm silica gel plates eluted in 2:1 hexane:ethyl acetate afforded 40 mg of 4''-vinyl -5-O-tert-butyldimethylsilyl avermectin B1a/1b characterized by its NMR and mass spectra.

200 MHz NMR: δ0.15 (s), 0.96 (s), 1.14 (d, J=6 Hz), 1.20 (d, J=7 Hz), 1.27 (d, J=6 Hz), 1.53 (s), 1.82 (s), 1.78–2.40 (m), 2.56 (m), 3.25 (t, J=9 Hz), 3.43 (s), 3.48 (s), 3.60 (m), 3.90 (m), 4.17 (s), 4.44 (br d), 4.68 (ABq, J=15 Hz), 4.81 (d, J=3 Hz), 5.04 (m), 5.32 (dd, J=3, 10 Hz), 5.45 (m), 5.52 (d, J=2 Hz), 5.60 (dd, J=3, 10 Hz), 5.80 (m).

EXAMPLE 18b

4''-Vinylavermectin B1a/1b

To a solution of 35 mg of 4''vinyl 5-O-tert-butyldimethylsilylavermectin B1a/1b in 2 mL of freshly distilled THF at 22° C. in a polypropylene vial under nitrogen was added 2 mL of a solution of hydrogen fluoride pyridine in THF (prepared by diluting 10 mL of commercially available HF-pyridine complex with 20 mL of dry pyridine and 70 mL of THF). The mixture was stirred at 22° C. for 16 hours. The reaction was then diluted with ice water, the HF was neutralized with aqueous sodium bicarbonate and the organic product was extracted with ether. The ethereal extracts were combined and dried over MgSO$_4$, evaporated in vacuo to yield a glossy solid. Preparative layer chromatography on a 0.05 mm thick silica gel plate eluted in 50% ethyl acetate-hexane afforded 31 mg of 4''-vinylavermectin B1a/1b characterized by its NMR and mass spectra.

EXAMPLE 19a

4''-butyl-5-O-tertbutyldimethylsilylavermectin B1a/1b

To 210 mg of CuBr.SMe$_2$ in a dry flask under nitrogen was added 8 mL of distilled ether. The slurry was cooled to 0° C. and 0.80 mL of a 2.5 M n-butyllithium solution in hexane was added dropwise. A dark red solution was obtained. A solution of 100 mg of 4''-oxo-5-O-tert-butyldimethyl silylavermectin B1a/1b in 0.5 mL of THF was then added dropwise to the chilled (0° C.) lithium cuprate solution. After 30 min the reaction was stopped by the addition of 5 mL of saturated aqueous ammonium chloride solution. The mixture was extracted with ether and evaporation of the dried (MgSO$_4$) ethereal extracts provided a glossy solid. Preparative thin layer chromatography on silica gel provided 60 mg of 4''-butyl-5-O-tertbutyldimethylsilyl avermectin B1/1b characterized by its NMR and mass spectra.

200 MHz NMR: 0.15 (s), 0.97 (s), 1.20 (d, J=7 Hz), 1.26 (d, J=6 Hz), 0.80–1.80 (m), 1.54 (s), 1.83 (s), 1.80–2.40 (m), 2.56 (m), 3.30 (t, J=91 Hz), 3.44 (s), 3.48 (s), 3.60 (m), 3.87 (d, J=6 Hz), 3.96 (m), 4.17 (s), 4.48 (br s), 4.68 (ABq J=15 Hz), 4.81 (d, J=4 Hz), 5.06 (m), 5.38 (s), 5.40 (m), 5.46 (d, J=3 Hz), 5.60 (dd, J=3, 10 Hz), 5.80 (m).

EXAMPLE 19b

4''-n-Butylavermectin B1a/1b

To a solution of 55 mg of 4''-n-butyl-5-O-tert-butylavermectin B1a/1b in 2 mL of THF was added 2 mL of hydrogen fluoride-pyridine in THF solution (prepared as described in Example 18b). The mixture was stirred in a polypropylene vessel for 16 hours under anhydrous nitrogen. The reaction was then worked up by the addition of ice water, aqueous sodium bicarbonate solution, and extraction with ether. Evaporation of the ether solvent and preparative layer chromatography of the residual solid on a 0.1 mm silica gel plate eluted in 50% ethyl acetate-hexane provided 45 mg of 4''-n-butylavermectin B1a/1b characterized by its NMR and mass spectra.

EXAMPLE 20a

5-O-t-Butyldimethylsilyl-13-deoxyavermectin B2a and/or B2b Aglycone

A solution of 324 mg (0.55 mmole) of 13-deoxyavermectin B2a and/or B2b aglycone, 240 mg of imidazole and 240 mg of tert-butyldimethylsilyl chloride in 4 ml of anhydrous DMF is stirred at room temperature for 50 minutes. Then the reaction mixture is poured into 150 ml of ice cold water and the aqueous phase is extracted four times with 20 ml of ether. The organic phase is washed twice with water, aqueous NaCl solution, dried with MgSO$_4$ and concentrated in vacuo to a white foam. The crude product is purified by silica gel column chromatography with a CH$_2$Cl$_2$-EtOAc-90:10 to 70:30 solvent system to give 5-O-t-butyldimethylsilyl -13-deoxyavermectin B2a and/or B2b aglycone as an amorphous foam, which is characterized by its $^1$H-NMR and mass spectra.

EXAMPLE 20b

5-O-t-Butyldimethylsilyl-13-deoxy-23-oxoavermectin B2a and/or B2b Aglycone

To a solution containing 0.091 ml of oxalyl chloride in 2.3 ml of dry $CH_2Cl_2$ stirred at $-60°$ C. is added 0.015 ml of dry dimethylsulfoxide dissolved in 1.2 ml of dry $CH_2Cl_2$ during 15 min. Then a solution of 320 mg (0.46 mmole) of 5-O-t-butyldimethylsilyl-13-deoxyavermectin B2a and/or B2b aglycone dissolved in 2.3 ml of dry $CH_2Cl_2$ is added over a period of 15 minutes while maintaining the temperature at 60° C. The reaction mixture is stirred at this temperature for 30 minutes when 0.065 ml of dry triethylamine is added. The mixture is stirred for 5 additional minutes at $-60°$ C., and then the cooling bath is removed and the reaction mixture is allowed to come to ambient temperature. After addition of water the reaction product is extracted with $CH_2Cl_2$, the extract is washed with water, dried and concentrated in vacuo to a yellow foam. This is identified by its mass and NMR spectra as 5-O-t-butyldimethylsilyl-13-deoxy 23-oxoavermectin B2a and/or B2b aglycone, which is used for further chemical reactions without purification.

EXAMPLE 20c

5-O-t-Butyldimethylsilyl-13-deoxy-23-methylavermectin B2a and/or B2b Aglycone A solution of 195 mg (0.28 mmole) of 5-O-t-butyl-dimethylsilyl-13deoxy-23-oxoavermectin B2a and/or B2b aglycone in 12 ml of anhydrous tetrahydrofuran is stirred under $N_2$ at room temperature while 0.5 ml of 2.85 molar methylmagnesium bromide solution in ether is added dropwise from a syringe. After 1 hour the reaction mixture is poured onto 60 ml of a 10% aqueous ammonium chloride solution, and the product is extracted with EtOAc. The extract is washed with water, dried over $MgSO_4$, and concentrated in vacuo to a yellow glass. This is purified by preparative silica gel layer chromatography with $CH_2Cl_2$ containing 3 to 5% of MeOH to give a white foam, which is characterized as 5-O-t-butyldimethylsilyl-13deoxy-23-methylavermectin B2a and/or B2b aglycone by its mass spectrum and $^1$H-NMR spectrum.

EXAMPLE 20d

13-Deoxy-23-methylavermectin B2a and/or B2b Aglycone

A solution of 250 mg (0.34 mmole) of crude 5-O-t-butyldimethylsilyl 13-deoxy -23-methylavermectin B2a and/or B2b aglycone and 250 mg of p-toluene sulfonic acid in 25 ml of MeOH is held at room temperature for 35 minutes and then poured into 65 ml of dilute aqueous $NaHCO_3$ solution. The product is extracted with ether and EtOAc. The extract is washed with water, saturated aqueous NaCl, dried over $MgSO_4$, and concentrated in vacuo to a yellow foam. Purification by preparative silica gel thin layer chromatography with a $CH_2Cl_2$-EtOAc 85:15 solvent mixture affords the pure 13-deoxy-23-methylavermectin B2a and/or B2b aglycone, which is characterized by its mass and $^1$H-NMR spectra.

PREPARATION OF STARTING MATERIALS

PREPARATION 1

23-Oxo-avermectin B2a/B2b

23 -Oxo-avermectin B2a/B2b was prepared as described by V. P. Gallo et al. in *Pestic. Sci.* 1983, 4, 153–157, and in U.S. Pat. No. 4,289,760: 23 Keto derivatives of C-076 compounds, ex. 2,4,5).

PREPARATION 2

23-Oxo-avermectin B2a/B2b Monosaccharide

A solution of 190 mg of 23-oxo-avermectin B2a/B2b in 6.0 ml of i propanol containing 0.06 ml of concentrated sulfuric acid was left for 18 hours at room temperature. Then dilute aqueous $NaHCO_3$ solution was added, and the product was extracted with EtOAc, washed with water, and dried and concentrated to 170 ml of light glass. Purification by preparative silca gel layer chromatography with 1:1 $CH_2Cl_2$EtOAc solvent mixture gave 75 mg of 23-oxo avermectin B2a/B2b monosaccharide, which was characterized by its mass, $^1$H—, NMR and UV spectra.

PREPARATION 3a

5-O-t-butyl-dimethylsilyl-22,23-dihydro avermectin B1a/B1b 3 g of 22,23-dihydro avermectin B1a/B1b in 0 ml of dry dimethylformamide was combined with 1.4 g of imidazole and stirred at room temperature until all the materials had dissolved. Then 1.56 g of t-butyl-dimethylsilyl chloride was added and the reaction mixture stirred at room temperature for 70 minutes. The reaction mixture was diluted with 150 ml. of ether, water was added and the layers were separated. The aqueous layer was extracted twice more with ether and the combined ether layers washed four times with water and once with saturated sodium chloride solution. The ether layer was dried over magnesium sulfate and concentrated to dryness in vacuo affording 4.2 g of a white foam. The foam is chromatographed on 135 g. of 70–230 mesh silica gel and eluted with 5% tetrahydrofuran in methylene chloride. 1.15 G of 4''-5-di-O-t-butyl-dimethylsilyl 22,23 dihydro avermectin B1a/B1b and 2.6 g of 5-O-t-butyl dimethylsilyl-22,23-dihydro avermectin B1a/B1b were recovered as pure amorphous foams.

PREPARATION 3b

5-O-t-butyl-dimethylsilyl 4''-keto-22,23-dihydro avermectin B1a/B1b

In a dried flask purged with dry nitrogen was placed 97 µl of oxalyl chloride and 1.5 ml of methylene chloride. The reaction mixture was cooled to $-60°$ C., 1 ml of the methylene chloride solution containing 160 µl of dimethylsulfoxide was added over a period of 3 minutes and the reaction mixture stirred at $-60°$ C. for two minutes. 3 Ml of methylene chloride containing 500 mg of 5-O-t-butyl-dimethylsilyl 22,23-dihydro avermectin B1a/B1b was added dropwise over a period of 5 minutes and the reaction mixture stirred at room temperature for 30 minutes. At the end of this period, 0.71 ml of triethylamine was added dropwise and the reaction mixture was stirred at $-60°$ C. for 5 minutes. The cold bath was removed and the reaction mixture was allowed to come to room temperature over a period of 45 minutes. 50 Ml of water was added and the reaction mixture was extracted 3 times with 40 ml of ether. The ether extracts were combined and washed 4 times with 20 ml of water, dried over magnesium sulfate and concentrated to dryness in vacuo affording 520 mg of a yellow glass. The yellow glass was dissolved in methylene chloride and placed on three 2,000μ silica gel preparative layer chromatography plates. The plates were developed with 10% ethyl acetate in methylenechloride and afforded 470 ml of yellow foam which was characterized by its 300 MHz nuclear magnetic resonance spectrum as 5-O-t-butyl dimethyl-silyl-4‴-keto-22,23-dihydro avermectin B1a/B1b.

PREPARATION 3c

4‴-Keto-5-O-t-butyldimethylsilylavermectin B1a/B1b

If avermectin B1a/B1b is reacted according to the procedures of Preparation 3a and 3b, 4‴-keto-5-O-t-butyldimethylsilylavermectin-B1a/B1b is obtained.

PREPARATION 3d

4‴-Keto-avermectin B1a/B1b

If the product of Preparation 3c is reacted according to the procedures of Example 17f, 4‴-keto- avermectin B1a/B1b is obtained.

PREPARATION 4a

4‴-Keto-5-O-t-butyldimethylsilyl-22,23-dihydroavermectin B1a/B1b monosaccharide

If 22,23-dihydroavermectin B1a/B1b-monosaccharide is reacted according to the procedures of Preparations 3a and 3b, 4′-keto-5—O-t-butyldimethylsilyl-22,23-dihydroavermectin B1a/B1 b monosaccharide is obtained.

PREPARATION 4b

4‴-Keto-22,23-dihydroavermectin B1a/B1b monosaccharide

If the product of preparation 4a is reacted according to the procedures of Example 17f 4′-keto-22,23-dihydroavermectin B1a/B1b monosaccharide is obtained.

PREPARATION 5

22,23-dihydro-5-oxo-avermectin B1a/B1b 22,23-dihydro 5oxo avermectin B1a/B1b was prepared as described by J. D. Stong Anal. Chem. 1987, 59, 266–270 and J. C. Chabala et al. J Agric. Food Chem. 1981, 29, 881–884.

PREPARATION 6

5-O-tert-Butyldimethylsilyl-22,23-dihydro avermectin B1a and/or B1b aglycone

5-O-tert-Butyldimethylsilyl-22,23-dihydro avermectin B1a and/or B1b aglycone was prepared as described by H. Mrozik et al. Tetrahedron Lett. 1983, 24, 5333–5336.

PREPARATION 7

5-O-tert-Butyldimethylsilylavermectin B2a/B2b aglycone

A solution of 400 mg of avermectin B2a/B2b aglycone (described by G. Albers-Schonberg et al. J. Am. Chem. Soc. 1981, 103, 4216–4221) in 8.0 ml of DMF was treated with 544 mg of imidazole and 600 mg of tert-butyldimethylsilyl-chloride and stirred at room temperature for 50 minutes. Then water was added and the product was extracted with ether. The ether extracts were washed repeatedly with water, dried and concentrated in vacuo to 800 mg of a light foam. Purification by preparative silica gel layer (2 mm thickness) chromatography with 95:5 $CH_2Cl_2$-THF solvent mixture gave 138 mg of 5,23-O-tert-butylimethylsilylavermectin B2a and/or B2b aglycone and 330 mg of the desired 5-O-tert-butyldimethylsilylavermectin B2a and/or B2b aglycone, which were characterized by their mass and $^1$H-NMR spectra.

PREPARATION 8

5-O-tert-Butyldimethylsilyl-13-beta-chloro-13-deoxyavermectin B2a and/or B2b aglycone A solution of 150 mg of 5-O-tert-butyldimethylsilylavermectin B2a and/or B2b aglycone (obtained in Preparation 7), 40 mg of 4-dimethylaminopyridine, 0.3 ml (=222 mg) of N,N-diisopropylethylamine in 5.0 ml of anhydrous $CH_2Cl_2$ stirred at room temperature was treated with a solution of 286 mg of 2-nitrobenzenesulfonyl chloride in 0.5 ml of anhydrous $CH_2Cl_2$. After 3 hours water was added and the product was extracted with $CH_2Cl_2$. The extract was washed with water, dried and concentrated in vacuo to 300 mg of an orange colored solid. Purification by preparative silica gel layer chromatography using $CH_2Cl_2$ containing 4% of THF and 0.1% of ethanol as solvent gave 88 mg of 5″-O-tert-butyldimethylsilyl-13-beta chloro-13-deoxyavermectin B2a and/or B2b aglycone as a yellow glass, which was characterized by its mass and 300 MHz $^1$H-NMR spectra.

PREPARATION 9

5-O-tert-Butyldimethylsilyl-13-deoxyavermectin B2a and/or B2b aglycone

A solution of 67 mg of 5-O-tert-butyldimethylsilyl-13-beta chloro-13-deoxyavermectin B2a and/or B2b aglycone and 20 mg of 2,2′-azobis(2-methylpropionitrile) in 1.5 ml of tributyltin hydride was stirred for 3.3 hours at 85° C. It was cooled to room temperature, diluted with $CH_2Cl_2$ and poured through a column containing 50 g of silica gel. Several column volumes of $CH_2Cl_2$ were used to wash off the tin compounds. Then EtOAc was used to elute the product. Evaporation of the solution to dryness in vacuo gave 100 mg of crude 5-O-tert-butyldimethylsilyl-13-deoxyavermectin B2a and/or B2b aglycone, which was characterized by its mass spectrum. Further purification is achieved using preparative silica gel layer chromatography.

What is claimed is:

1. A compound having the formula:

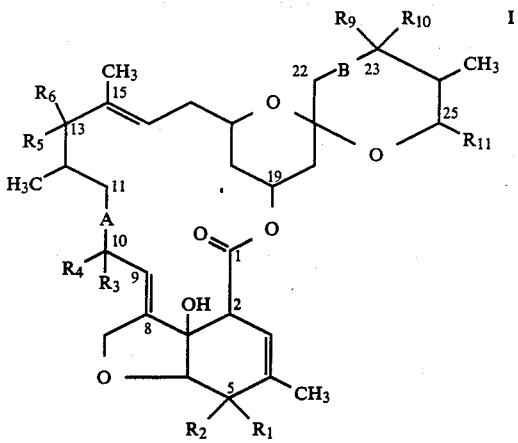

wherein A and B are independently single or double bonds;
  wherein $R_1$ is hydroxy, $R_2$ is loweralkyl, cycloloweralkyl, loweralkenyl or substituted loweralkyl;
  or when $R_1$ is hydrogen, $R_2$ is hydroxy or methoxy;
  when A is a double bond $R_4$ is not present and $R_3$ is hydrogen or loweralkyl;
  when A is a single bond $R_3$ is hydroxy and $R_4$ is loweralkyl, cycloloweralkyl, loweralkenyl or substituted loweralkyl;
  when $R_5$ is hydroxy, $R_6$ is loweralkyl, cycloloweralkyl, loweralkenyl or substituted loweralkyl;
  or when $R_5$ is hydrogen $R_6$ is hydrogen, halogen, hydroxy,

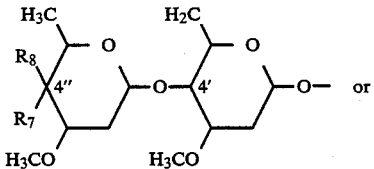

when $R_7$ is hydroxy and $R_8$ is loweralkyl, cycloloweralkyl, loweralkenyl, cycloloweralkyl, or substituted loweralkyl; or when $R_7$ is hydrogen, $R_8$ is hydroxy, amino, loweralkylamino, diloweralkylamino, loweralkanoylamino, or loweralkenoyl (loweralkyl) amino;
  when B is a single bond, $R_9$ is hydroxy and $R_{10}$ is loweralkyl, cycloloweralkyl, loweralkenyl, or substituted loweralkyl;
  or $R_9$ is hydrogen and $R_{10}$ is hydrogen or hydroxy;
  when B is a double bond $R_1$ is not present and $R_9$ is hydrogen; and
  $R_{11}$ is methyl, ethyl, isopropyl, sec. butyl, or $C(CH_3)=C.HCH_3$, $-C(CH_3)=C.HCH_2CH_3$ or $-C(CH_3)=C.HCH(CH_3)_2$;
  provided that when $R_1$, $R_5$, $R_7$ and $R_9$ are all hydrogen and A is a double bond, $R_4$ is not present and $R_3$ is loweralkyl or provided that at the disubstituted positions 5, 10, 13, 23, 4 and 4" the combination is present whereby at least one of $R_1$, $R_3$, $R_5$, $R_7$, and $R_9$ is hydroxy and the corresponding $R_2$, $R_4$, $R_6$, $R_8$, and $R_{10}$ is loweralkyl, cycloloweralkyl, loweralkenyl or substituted loweralkyl and the substituent on the substituted lower alkyl groups are one or more of hydroxy, loweralkoxy or halogen.

2. The compound of claim 1 wherein
  A is a double bond;
  B is a single or a double bond;
  $R_1$ is hydrogen;
  $R_2$ is hydroxy or methoxy;
  $R_3$ is hydrogen and $R_4$ is not present;
  $R_5$ is hydrogen;
  $R_6$ is hydrogen, hydroxy,

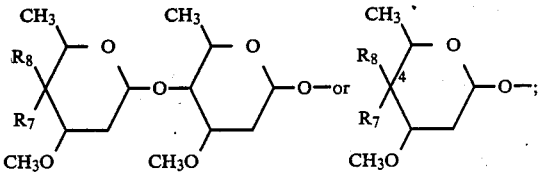

$R_7$, $R_8$, $R_9$ and $R_{10}$ are as defined in claim 1; and $R_{11}$ is methyl, ethyl, isopropyl or sec-butyl.

3. The compound of claim 1 wherein
  A is a double bond;
  B is a single or a double bond;
  $R_1$ and $R_2$ are defined in claim 1;
  $R_3$ is hydrogen and $R_4$ is absent;
  $R_5$ is hydrogen;
  $R_6$ is

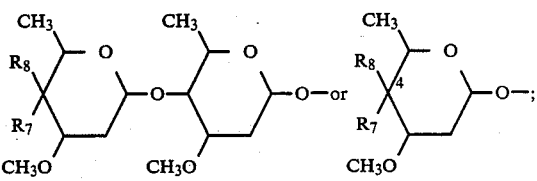

$R_7$, $R_8$, $R_9$ and $R_{10}$ are as defined in claim 1; and $R_{11}$ is isopropyll or sec-butyl.

4. The compound of claim 1 which is 4"-methylavermectin B1a or B1b.

5. The compound of claim 1 which is 22,23-dihydro-4"-methylavermectin B1a or B1b.

6. The compound of claim 1 which is 4"-(n-butyl)avermectin B1a or B1b.

7. The compound of claim 1 which is 4"-methylavermectin B2a or B2b.

8. The compound of claim 1 which is 23-methylavermectin B2a or B2b.

9. The compound of claim 1 which is 13-deoxy-23-methylavermectin B2a or B2b aglycone.

10. The compound of claim 1 which is 4"'-deoxy-4"-methylamino-23-methyl avermectin B2a or B2b.

11. The compound of claim 1 which is 10-methylavermectin B1a or B1b.

12. A method for the treatment of parasitic infections in animals which comprises administering to such animals an effective amount of a compound of claim 1.

13. A method for the treatment of pest infections of agricultural crops which comprises applying to such crops or the soil in which they grow, an effective amount of a compound of claim 1.

14. A composition useful for the treatment of parasitic infections in animals and for the treatment of pests of agricultural crops which comprises an inert carrier and an effective amount of a compound of claim 1.

* * * * *

UNITED STATES PATENT AND TRADEMARK OFFICE
CERTIFICATE OF CORRECTION

PATENT NO. : 4,906,619

DATED : March 6, 1990

INVENTOR(S) : Philip Eskola, T.L. Shih, H. Mrozik

It is certified that error appears in the above-identified patent and that said Letters Patent is hereby corrected as shown below:

In Column 9, line 9, delete "nd" and insert therefor -- and --

In Column 7, line 29, delete "ide" and insert therefor -- side --

Signed and Sealed this

Twenty-third Day of July, 1991

Attest:

HARRY F. MANBECK, JR.

Attesting Officer

Commissioner of Patents and Trademarks